United States Patent [19]

Rajala et al.

[11] Patent Number: 4,756,183
[45] Date of Patent: Jul. 12, 1988

[54] METHOD AND APPARATUS FOR MEASURING AIR PERMEABILITY OF A WALL-LIKE OR SHEET-LIKE ELEMENT

[75] Inventors: Raimo Rajala, Kaarina; Raimo Virta, Turku, both of Finland

[73] Assignee: Valmet Oy, Finland

[21] Appl. No.: 36,596

[22] Filed: Apr. 18, 1987

[30] Foreign Application Priority Data

Apr. 10, 1986 [FI] Finland ............................... 861534

[51] Int. Cl.⁴ ............................................ G01N 15/08
[52] U.S. Cl. ........................................ 73/38; 73/37.7
[58] Field of Search ......................... 73/38, 37.7, 37.6

[56] References Cited

U.S. PATENT DOCUMENTS

| | | | |
|---|---|---|---|
| 3,808,876 | 5/1974 | Kershaw | 73/38 |
| 4,311,037 | 1/1982 | Gotchel et al. | 73/37.7 X |
| 4,401,147 | 8/1983 | Beck et al. | 73/38 X |
| 4,536,971 | 8/1985 | Pulsmeier et al. | 73/38 X |
| 4,676,091 | 6/1987 | Schuster et al. | 73/37.7 X |

FOREIGN PATENT DOCUMENTS 2095411  9/1982  United Kingdom ............... 73/38

Primary Examiner—Stewart J. Levy
Assistant Examiner—Joseph W. Roskos
Attorney, Agent, or Firm—Steinberg & Raskin

[57] ABSTRACT

Method and Apparatus for Measuring Permeability to Air of a Wall-Like or Sheet-Like Element, comprising the use of a measurement head including a blower having an air-discharge nozzle, a blade wheel and a variable-speed motor for rotating the wheel to produce an air flow which discharges through the nozzle. Pressure in the blower and speed of blade wheel rotation are detected, with appropriate signals indicative thereof being input to a central unit which then appropriately adjusts speed of rotation of the blade wheel to correspond to a predetermined blower pressure value. Permeability value of the element is then determined at the central unit, based on relationship between the speed measurement signal values, and corresponding permeability values.

16 Claims, 3 Drawing Sheets

METHOD AND APPARATUS FOR MEASURING AIR PERMEABILITY OF A WALL-LIKE OR SHEET-LIKE ELEMENT

BACKGROUND OF THE INVENTION

The present invention relates generally to methods and apparatus for measuring the air permeability of wall-like or sheet-like elements, such as a felt or wire used in paper machines.

In particular, the invention relates to air permeability measurement methods and apparatus wherein a measurement head including a blower having an air discharge nozzle, a blade wheel and a motor for rotating the blade wheel is used and wherein the measurement head is situated with the blower nozzle tightly engaging one of the surfaces of the element whose permeability is to be measured whereupon a volumetric air flow through the element is produced.

Measurement of the air permeability of various air permeable fabrics is often required. For example, the permeability of felts and drying wires of the type used in paper machines, filter elements, and the like, must be measured on a periodic basis to ascertain their condition. Such air permeability measurements must be performed in industrial environments and usually on the very sites at which the elements are used. For example, permeability meters are usually part of the standard equipment of every paper mill so that the permeability of plastic wires used in the paper machines can be measured periodically. Such plastic wires tend to become obstructed by dust or other contaminants or through a reduction in the mesh size of the wire screen during use. The machine operators must be aware of the fabric permeability since it is extremely important, such as in the case of drying wires of paper machines, to maintain a certain minimum permeability to assure proper operation of, for example, pocket ventilation devices and the like. A wire of a paper machine or a filter fabric of a filter device must be replaced or cleaned based on the permeability measurements. The proper operation of fabric cleaning or washing devices is also monitored through the measurement of the permeability of the elements upon which such devices operate.

SUMMARY OF THE INVENTION

Accordingly, an object of the present invention is to provide new and improved methods and apparatus for measuring the permeability to air of wall-like or sheet-like elements such, as wires or fabrics used in paper machines.

Another object of the present invention is to provide new and improved methods and apparatus for measuring air permeability of wall-like or sheet-like elements which are easier to operate, quicker and more precise than conventional methods and apparatus.

Still another object of the present invention is to provide new and improved methods and apparatus for measuring air permeability of wall-like or sheet-like elements, such a felts or wires used in paper machines, while the elements are situated in their operating locations.

A further object of the present invention is provide new and improved methods and apparatus for measuring air permeability of wall-like or sheet-like elements which can be utilized in cramped and congested locations.

Yet another object of the present invention is to provide new and improved apparatus for measuring air permeability of wall-like or sheet-like elements which can be transferred from one place of measurement to another in an easy manner.

Another object of the present invention is to provide new and improved methods and apparatus for measuring air permeability of wall-like or sheet-like elements which can be used to measure permeability values over wide ranges.

Still another object of the invention is to provide new and improved methods and apparatus for measuring air permeability of wall-like or sheet-like elements which comply with current standards of permeability measurement, particularly for measuring permeability of drying wires of paper machines.

Briefly, in accordance with the present invention, these and other objects are attained by providing a method including the steps of locating the blower with the discharge nozzle against one of the surfaces of the element, operating the motor to rotate the blade wheel to produce a volumetric air flow through the thickness of the element and a corresponding pressure in the blower, detecting the pressure in the blower and generating a pressure measurement signal indicative of the magnitude of the detected pressure which is input to the central unit, and, at the same time, detecting the speed of rotation of the blade wheel of the blower and generating a speed measurement signal indicative of the magnitude of the blade wheel rotational speed which is input to the central unit, adjusting the speed of rotation of the blade wheel through the central unit by adjusting the speed of the motor until the blower pressure is substantially equal to a pre-determined standard value at which time the speed measurement signal input to the central unit corresponds to the pre-determined standard blower pressure, and determining the permeability value of the element at the central unit based on a previously determined relationship between the values of speed measurement signals corresponding to the predetermined standard blower pressure and corresponding permeabilities.

According to the invention, apparatus are provided comprising a measurement head including a blower having an air discharge nozzle, a blade wheel and a variable-speed motor for rotating the blade wheel to produce an air flow which discharges through the nozzle, means for detecting the speed of rotation of the blade wheel and for generating a speed measurement signal indicative of the magnitude of the blade wheel rotational speed, means for detecting pressure in the measurement head and for generating a pressure measurement signal indicating of the magnitude of the pressure, a central unit operatively coupled to the measurement head, means for inputting the speed measurement signal and pressure measurement signal into the central unit, and wherein the central unit includes means for adjusting the speed of rotation of the blower motor until the blower pressure equals a predetermined standard blower pressure and for converting the value of the resulting speed measurement signal when then corresponds to the predetermined standard blower pressure to the value of the permeability of the element based on a previously determined relationship between the values of speed measurement signals corresponding to the predetermined standard pressures and corresponding permeabilities.

DESCRIPTION OF THE DRAWINGS

A more complete appreciation of the present invention and many of the attendant advantages thereof will readily understood by reference to the following detailed description when considered in connection with the accompaning drawings in which.

DESCRIPTION OF THE PREFERRED EMBODIMENTS

Figure 1:
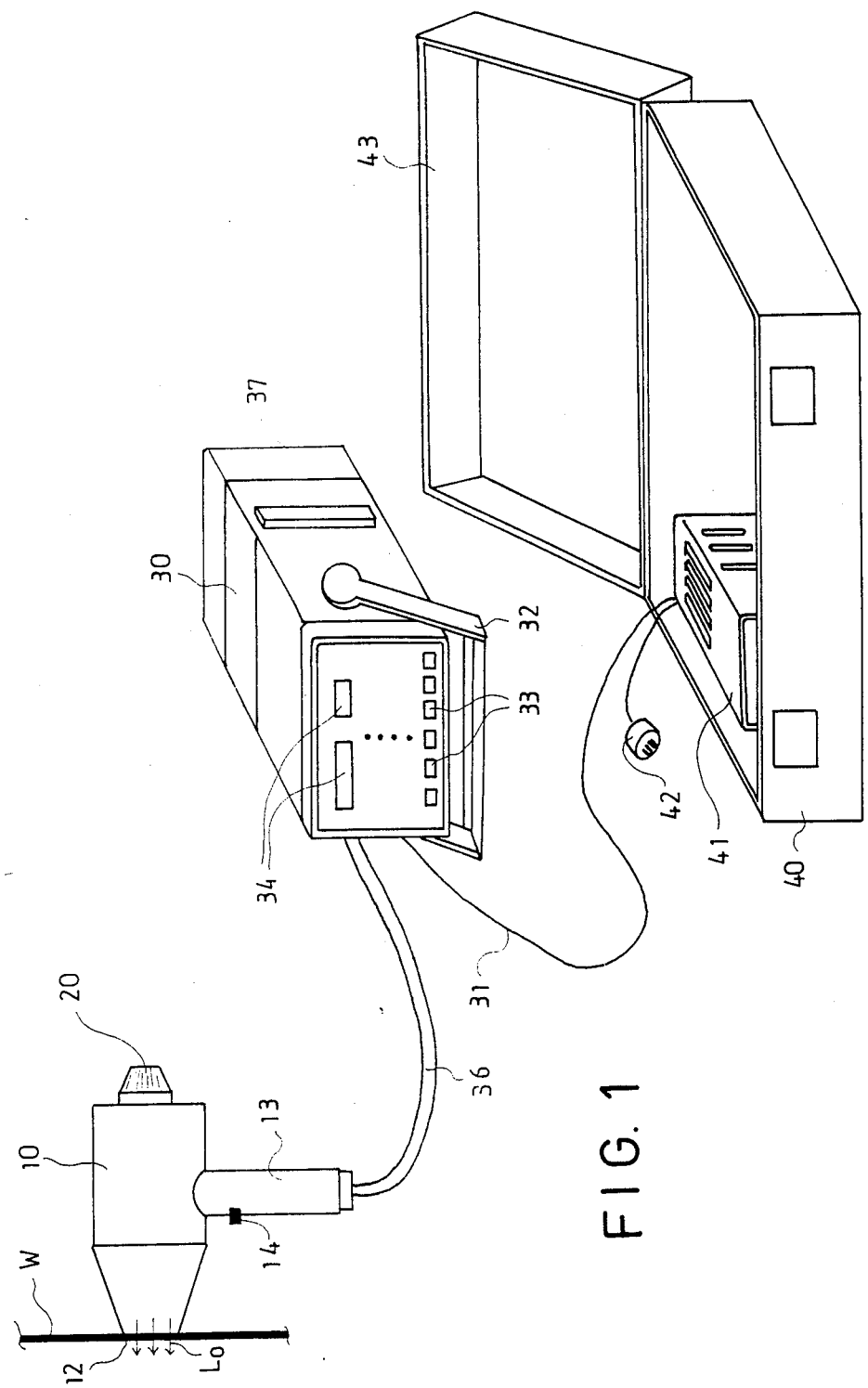
FIG. 1 is an axonometric view of apparatus in accordance with the invention and illustrating the method of the invention.

Referring now to the drawings wherein like reference characters designate identical or corresponding parts throughout the several views, and more particularly to FIG. 1, measurement apparatus in accordance with the invention comprises a measurement head 10 coupled to a central unit 30 by an electric cable 36. The central unit 30 is provided with display windows 34 for displaying measurement results and with keys 33 for setting and controlling the measurement operation. A transportation bag 40 is provided for the equipment in which an electrical recharging device 41 is contained which is adapted to be connected to a supply of electricity through its own line and plug 42. The recharging device 41 provides a charging voltage of, for example, 20 volts to an accumulator unit 37 in the central unit 30 and also to the motor 16 (FIG. 2) of the measurement head 10 by way of cable 36. The central unit 30 is provided with a carrying handle 32. The transportation box 40 is provided with a closeable lid 43 and is large enough to accommodate the measurement head 10 and central unit 30 so that the apparatus is easily transportable from one location to another.

Figure 2:
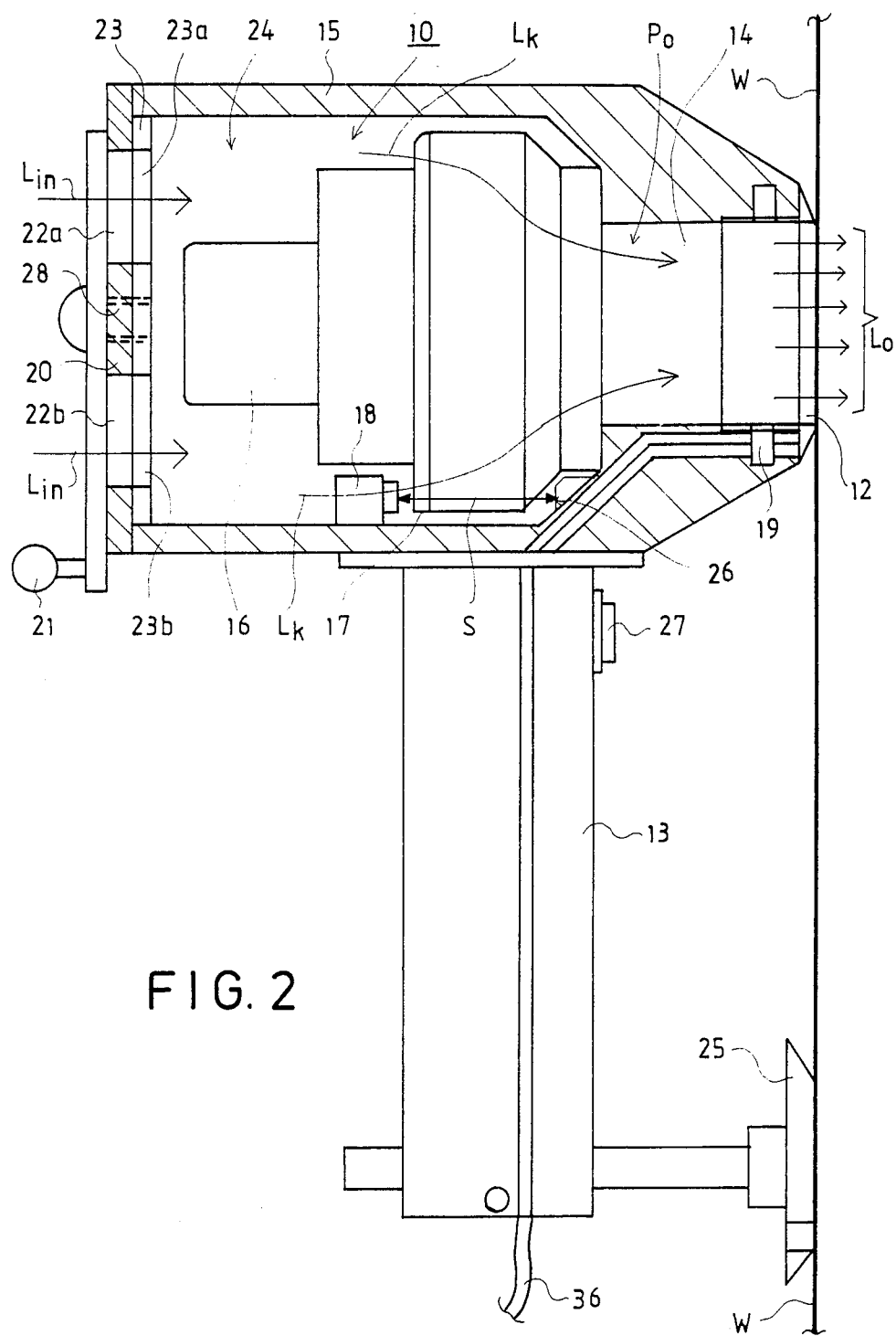
FIG. 2 is a side elevation view in partial section of a measurement head of apparatus in accordance with the invention shown in operating position.
Figure 3:
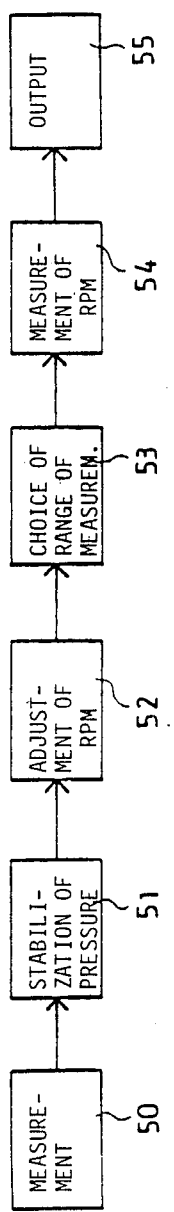
FIG. 3 is a block diagram illustrating the principle of a measurement method in accordance with the invention.

Referring now to FIGS. 2 and 3, a measurement head 10 in accordance with the invention resembles a handheld blower provided with a handle 13. The measurement head 10 comprises a substantially cylindrical housing 15 in which a blower is located. The blower includes a blower motor 16, preferably a DC motor whose rotational speed r can be regulated by adjusting the voltage applied to the motor. The voltage applied to the motor 16 is obtained from the accumulator 37 by way of the central unit 30 which is provided with conventional voltage regulating devices (not shown). The blower also includes a blade wheel 17 which is rotated by the variable-speed motor 16 so that when the blade wheel 17 is rotated by motor 16, an air flow is produced by the blades of the wheel suctioning air into the measurement head 10 in the direction of arrows $L_{in}$ through openings 22a, 23a and 22b, 23b.

A nozzle 12 is provided on the pressure side of the blade-wheel 17 and air flows from the suction space 24 behind blower wheel 17 in the direction of arrows $L_k$ into a substantially cylindrical pressure space 14 which communicates with the nozzle 12. The nozzle includes in the direction of air travel a first relatively deep netlike planar member in addition to an outer nozzle member which is adapted to be located in precise sealing engagement against the surface of the element whose permeability is to be measured. In the illustrated embodiment, the element comprises a wire W.

The measurement head 10 also includes a photoelectric detector 18 arranged in operative relationship with the blade wheel 17 by means of which the speed of rotation r of blade wheel 17 is detected. Detector 18 operates in the illustrated embodiment by transmitting a beam of light S onto a reflecting surface 26 which reflects the beam back to the detector 18. As the blade wheel 17 rotates, it interrupts the detector beam S so that the photoelectric detector 18 generates a pulse signal whose frequency f is proportional to the speed of rotation r of the blower. The pulse signal is thereby indicative of the magnitude of the blade wheel rotational speed and, according to the invention, the speed measurement signal is transmitted or input to the central unit 30 by means of cable 36. According to the invention, the speed of rotation r of the blade wheel 17 can be adjusted by regulating the speed of rotation of the motor 16.

The apparatus also includes means for detecting the pressure $P_o$ in the pressure space 14 in front of the blade wheel 17, and for generating a pressure measurement signal that it is indicative of the magnitude of the pressure and which is input to the central unit 30. In the illustrated embodiment, measurement head 10 includes a pressure opening 19 which communicates with the pressure space 14. The pressure $P_o$ in the pressure opening 19 is transmitted to a conventional pressure detector provided in the central until 30 through a hose provided within the cable 36. The pressure $P_o$ will vary (when the measurement method is carried out) as the speed of rotation of the motor 16 is adjusted. Thus, for a particular element whose permeability is to be measured, the speed of rotation r of motor 16 can be adjusted to obtain a desired pressure $P_o$. In accordance with the method of the invention, a particular pressure $P_o$ is predetermined to constitute a standard value, e.g., $P_o = 100$ Pa, for the case of measuring permeability of wires W for paper machines.

The measurement head 10 includes regulating means for selecting a range of permeability values at which it will be operated. In the illustrated embodiment, the regulating means comprises a disc 20 having openings 22a and 22b formed therein which is rotatably mounted on a shaft 28 at the intake side 24 of the blower. The disc 20 can be rotated by means of a crank 21 so that either or both openings 23a and 23b formed in the measurement head housing 15 is opened by aligning with one or both of the openings 22a and 22b of disc 20.

A handle 13 is connected to the housing 15 of the measurement head. A switch 27 is provided on the handle by means of which the permeability value shown in the display window of the central unit can be stored in the memory unit. The handle 13 further includes a stop 25 by means of which the nozzle 12 of the measurement head 10 can be positioned precisely in correct position against the element W during the measurement operation.

The operation of the apparatus in accordance with the invention will now be described. The method in essence initially comprises measuring and stabilizing of the pressure $P_0$ in the pressure space 14 of the blower, designated by the blocks 50 and 51 in the block diagram of FIG. 3. In particular, the measurement head is located as shown in FIG. 2 with the nozzle tightly engaging the surface of the wire W and the motor 16 operated to produce a volumetric air flow $L_0$ through the thickness of the wire and a corresponding pressure $P_0$ in the blower. The blower pressure is detected and a pressure measurement signal is derived at the central unit 30. At the same time, the speed of rotation r of the blade wheel is detected by detector 18 which generates a speed measurement signal indicative of the magnitude of the blade wheel rotational speed which is input through cable 36 to the central unit. The central unit 30 then operates to adjust the speed of rotation r of blade wheel 17 by adjusting the speed of motor 16 until the blower pressure $P_0$ is substantially equal to a predetermined standard value, e.g., $P_0=100$ Pa (see block 52 in FIG. 3). At this time, the speed measurement signal being input to the central unit 30 thus corresponds to the predetermined standard blower pressure. This stage of the method is represented by block 54 in FIG. 3. The value of the permeability of the element W can then be determined at the control unit 30 based on a previously determined relationship $P=f(r)$ between the values of the speed measurement signal corresponding to the predetermined standard blower pressure and corresponding permeabilities. Such relationships, which have been obtained such as by means of experimentation, are stored in the memory of the central unit either in the form a function or in the form of discrete values. For example, the central unit 30 may include a microprocessor which controls the operations described above as well as the generation of the output which is illustrated by the last block 55 in FIG. 3. The central unit can also include a memory unit for the storage of several measurement results. Thus, the permeability value of the element W is determined at the control unit 30 for the particular speed r of the motor that corresponds to the predetermined standard blower pressure.

The measurement head 10 includes the devices 20, 21 and 28 by which the range of measurement of permeability values can be selected. For example, the apparatus may have two ranges of measurement, namely, a first range A extending from about 0 to about 1000 $m^3/h/m^2$, and a second range of measurement B extending from about 1000 to about 12000 $m^3/h/m^2$. Referring to the curve $P=f(r)$ in FIG. 4, the vertical axis A corresponds to the first range of measurement and the vertical axis B corresponds to the second range of measurement. When the apparatus is adjusted for the first range of measurement A, only one of the openings 22a or 22b in the wall 23 of the intake side 24 of the blower is opened. When the second range of measurement B is selected, both of the openings 23a and 23b are opened, as shown in FIG. 2. The selection of the range of measurement (A/B) is illustrated by the block 53 in FIG. 3.

Figure 4:
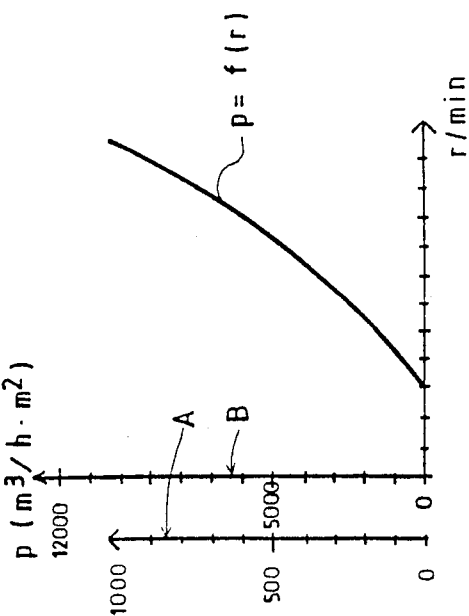
FIG. 4 is a graphical illustration showing a predetermined relationship between values of speed measurement corresponding to a predetermined standard blower pressure and corresponding permeabilities for two ranges of permeability values.

As noted above, the system of curves such as are shown in FIG. 4 and which constitutes a part of the invention are first measured by means of precise measurement equipment and the data obtained by such measurements are programmed into the central unit 30.

The central unit 30 may be connected with various processing and storage equipment by which the measured permeability can be used, for example, to determine average measurements over a certain time period, which average value can be displayed in display 35. The range of measurements is selected by means of the devices 20, 21, 22 in measurement head 10 and by means of the key 33 on the central unit 30.

A more accurate measurement is obtained using the method and apparatus of the invention compared to conventional arrangements since the speed of rotation r of the motor can be measured considerably more precisely than the pressure. On the other hand, the pressure detector used in the invention can be calibrated very accurately within the range of the particular standard blower pressure, e.g., $P_0=100$ Pa.

The method of the invention is also rendered extremely accurate by virtue of the fact that the efficiency of the blower motor 16 and other factors, such a friction and the like, do not affect the measurement results.

Obviously, numerous modifications and variations of the present invention are possible in the light of the above teachings. For example, the pressure detector provided within the central unit 30 may be replaced by a pressure detector situated within the measurement head 10 itself with the measurement signal generated thereby being transmitted through the cable 36 to the central unit 30. Accordingly, the invention may vary from that specifically described above within the scope of the claims appended hereto.

What is claimed is:

1. A method for measuring the permeability to air of a wall-like or sheet-like element having opposite surfaces defining the thickness of the element between them, such as a felt or wire used in paper machines, utilizing a blower including an air discharge nozzle, a blade wheel and variable-speed motor means for rotating said blade wheel to produce an air flow which discharges through said nozzle, comprising the steps of:
   locating said blower with said discharge nozzle against one of the surfaces of said element and operating said motor means to rotate said wheel to produce a volumetric air flow through the thickness of said element and a corresponding pressure in said blower;
   detecting said pressure in said blower, and generating a pressure measurement signal indicative of the magnitude of said pressure which is input to a central unit coupled to said blower and, at the same time,
   detecting the speed of rotation of said blade wheel of said blower and generating a speed measurement signal indicative of the magnitude of said wheel rotational speed which is input to said central unit;
   operating said central unit to adjust the speed of rotation of said blade wheel by adjusting the speed of said motor until said blower pressure is substantially equal to a predetermined standard value at which time said speed measurement signal input to said central unit corresponds to said predetermined standard blower pressure;
   determining the permeability value of the element at said central unit based on a previously determined relationship between the values of speed measurement signals corresponding to said predetermined standard blower pressure and corresponding permeabilities; and
   pre-programming said central unit with said relationship between the values of speed measurement signals corresponding to said predetermined standard blower pressure and corresponding permeabilities.

2. The method of claim 1 including the further step of displaying said determined permeability value by means of said central unit.

3. The method of claim 1 including the further step of storing said determined permeability value by means of said central unit.

4. The method of claim 1 including detecting said speed of rotation of said blade wheel by pulse signal generating means, said speed measurement signal comprising a pulse signal having a frequency proportional to the speed of rotation of said blade wheel.

5. The method of claim 1 including detecting said blower pressure and generating an electrical pressure measurement signal which is input to said central unit.

6. The method of claim 1 including detecting said blower pressure and generating a pneumatic pressure measurement signal which is input to said central unit.

7. The method of claim 1 wherein said predetermined standard blower pressure is about 100 Pa.

8. A method for measuring the permeability to air of a wall-like or sheet-like element having opposite surfaces defining the thickness of the element between them, such as a felt or wire used in paper machines, utilizing a blower including an air discharge nozzle, a blade wheel and variable-speed motor means for rotating said blade wheel to produce an air flow which discharges through said nozzle, comprising the steps of:
  locating said blower with said discharge nozzle against one of the surfaces of said element and operating said motor means to rotate said wheel to produce a volumetric air flow through the thickness of said element and a corresponding pressure in said blower;
  detecting said pressure in said blower, and generating a pressure measurement signal indicative of the magnitude of said pressure which is input to a central unit coupled to said blower and, at the same time, detecting the speed of rotation of said blade wheel of said blower and generating a speed measurement signal indicative of the magnitude of said wheel rotational speed which is input to said central unit;
  operating said central unit to adjust the speed of rotation of said blade wheel by adjusting the speed of said motor until said blower pressure is substantially equal to a predetermined standard value at which time said speed measurement signal input to said central unit corresponds to said predetermined standard blower pressure;
  determining the permeability value of the element at said central unit based on a previously determined relationship between the values of speed measurement signals corresponding to said predetermined standard blower pressure and corresponding permeabilities;
  pre-programming said central unit with the relationship between the values of speed measurement signals corresponding to said predetermined standard blower pressure and corresponding permeabilities for a first lower range of permeability measurements and for a second higher range of permeability measurements, said first lower range of permeability measurements having a lower value of about 0; and
  selecting a desired range of permeability measurements at said central unit.

9. The method of claim 8 wherein said first lower range of permeability measurements is from about zero to about 1000 $m^3/h/m^2$ and said second higher range of permeability measurements is from about 1000 to about 12000 $m^3/h/m^2$.

10. The method of claim 8 wherein said blower communicates with suction openings of adjustable size and including the further step of selecting a desired range of permeability measurements at said blower by adjusting the size of said suction openings.

11. Apparatus for measuring the permeability to air of a wall-like or sheet-like element having opposite surfaces defining a thickness of the element between them, such as a felt or wire used in paper machines, comprising:
  a measurement head including a blower having an air discharge nozzle, a blade wheel and variable-speed motor means for rotating said blade wheel to produce an air flow which discharges through said nozzle;
  means for detecting the speed of rotation of said wheel of said blower and for generating a speed measurement signal indicative of the magnitude of said blade wheel rotational speed;
  means for detecting pressure in said measurement head and for generating a pressure measurement signal indicative of the magnitude of said pressure;
  a central unit operatively coupled to said measurement head;
  means for inputting said speed measurement signal into said central unit;
  means for inputting said pressure measurement signal into said central unit;
  said central unit including means for adjusting the speed of rotation of said blower motor means until said pressure equals a predetermined standard blower pressure and means for converting the value of the speed measurement signal corresponding to said predetermined standard blower pressure to the value of the permeability of said element based on a previously determined relationship between the vlaues of speed measurement signals corresponding to said predetermined standard pressure and corresponding permeabilities;
  wherein said measurement head includes an outer housing having at least one air intake opening and further including means for regulating the size of said at least one intake opening.

12. The combination of claim 11 further including support means for locating said measurement head in operating position against the element with said discharge nozzle in tight engagement against one of said element surfaces.

13. The combination of claim 12 wherein said support means includes a handle and a stop connected to said handle.

14. The combination of claim 11 wherein said measurement head includes a series of intake openings and said regulating means comprises means for selectively covering and uncovering one or more of said openings to select a range of permeability measurements.

15. The combination of claim 11 wherein said central unit includes means for displaying the determined permeability.

16. The combination of claim 11 further including a transportation bag containing said measurement head, control unit and a source of direct current voltage.

* * * * *